(12) United States Patent
Blackadar

(10) Patent No.: US 7,768,415 B2
(45) Date of Patent: Aug. 3, 2010

(54) SENSOR DEVICE WITH PERSISTENT LOW POWER BEACON

(75) Inventor: Thomas P. Blackadar, Natick, MA (US)

(73) Assignee: Nike, Inc., Beaverton, OR (US)

( * ) Notice: Subject to any disclaimer, the term of this patent is extended or adjusted under 35 U.S.C. 154(b) by 523 days.

(21) Appl. No.: 11/529,046

(22) Filed: Sep. 28, 2006

(65) Prior Publication Data

US 2008/0079589 A1 Apr. 3, 2008

(51) Int. Cl.
*G08B 21/00* (2006.01)
*A61N 1/00* (2006.01)
*H02J 7/00* (2006.01)

(52) U.S. Cl. ............... 340/636.1; 340/636.19; 607/17; 607/30; 320/136

(58) Field of Classification Search ............ None
See application file for complete search history.

(56) References Cited

U.S. PATENT DOCUMENTS

| | | | |
|---|---|---|---|
| 5,686,896 A * | 11/1997 | Bergman | 340/636.1 |
| 6,441,587 B2 * | 8/2002 | Okada et al. | 320/136 |
| 6,641,533 B2 * | 11/2003 | Causey et al. | 600/300 |
| 2004/0027249 A1 * | 2/2004 | Heiser et al. | 340/636.1 |
| 2004/0039424 A1 * | 2/2004 | Merritt et al. | 607/29 |
| 2005/0080566 A1 * | 4/2005 | Vock et al. | 702/2 |
| 2006/0035590 A1 | 2/2006 | Morris et al. | |
| 2006/0226999 A1 | 10/2006 | Wu | |
| 2006/0267554 A1 * | 11/2006 | Cargonja et al. | 320/130 |

FOREIGN PATENT DOCUMENTS

TW 273770 8/2005

OTHER PUBLICATIONS

European Patent Application No. 07852437.8 Office Action dated Mar. 16, 2010.

* cited by examiner

*Primary Examiner*—Daniel Wu
*Assistant Examiner*—Fekadeselassie Girma
(74) *Attorney, Agent, or Firm*—Banner & Witcoff Ltd.

(57) ABSTRACT

One disclosed method involves providing a first device comprising a sensor configured to sense a stimulus experienced by the first device, a controller configured to process data received from the sensor and thereby obtain processed sensor data, a transmitter configured to wirelessly transmit the processed data from the first device to a second device, and a battery configured to supply power to at least the controller and the transmitter. The first device is operated in a first operational mode in which the sensor, the controller, and the transmitter are used at least occasionally to obtain and transmit processed data to the second device. When it is determined that the battery is in a low power condition, the first device is operated in a second operational mode wherein the sensor, controller, and transmitter are not used to obtain and transmit processed sensor data to the second device, but wherein the first device at least occasionally transmits a signal to the second device that indicates a low power condition of the battery.

19 Claims, 3 Drawing Sheets

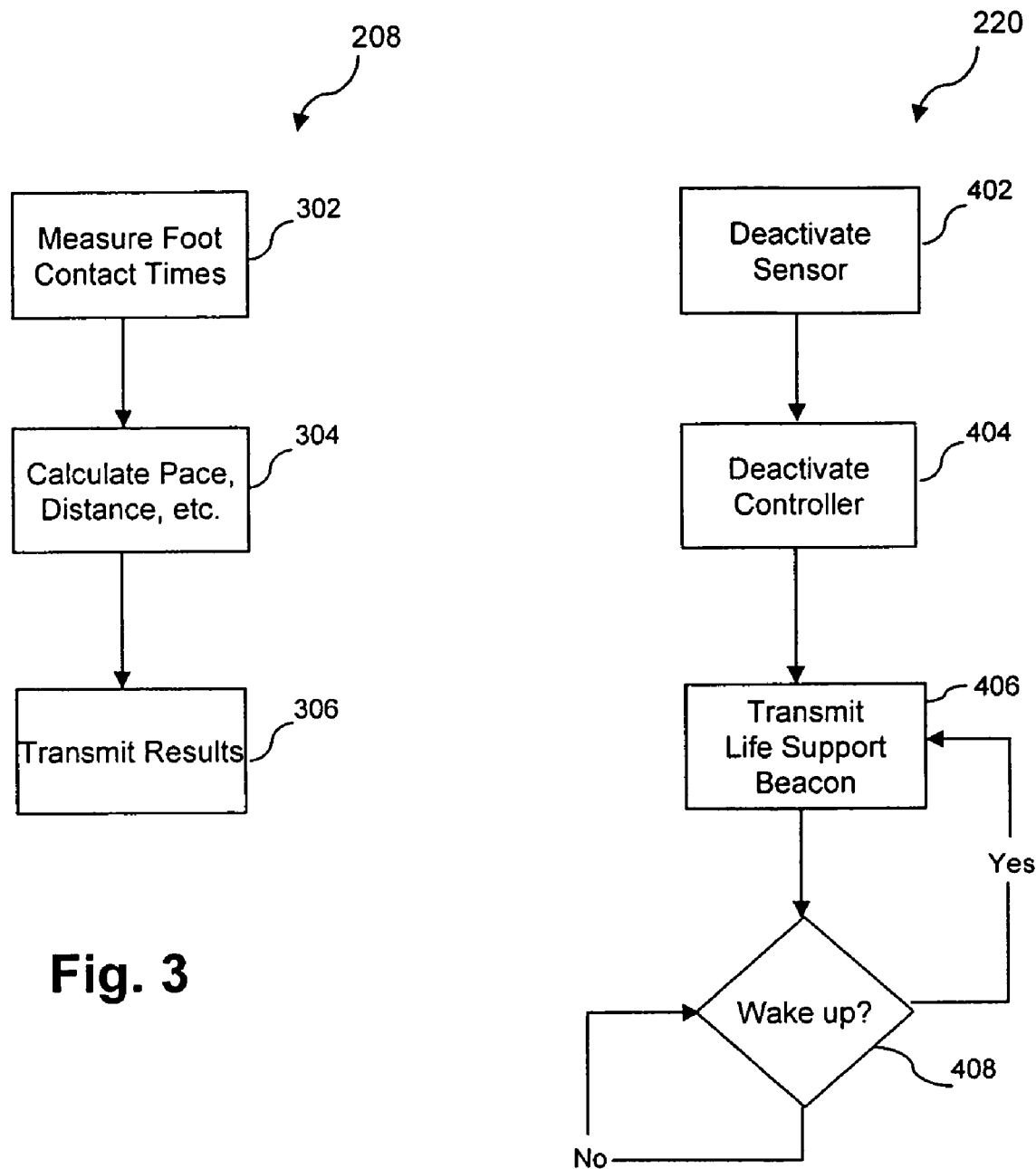

SENSOR DEVICE WITH PERSISTENT LOW POWER BEACON

FIELD

This application relates generally to power management of remote sensor devices.

BACKGROUND

Some remote sensor devices are capable of communicating a signal to a primary device indicating when the remote device is low on power. Upon receiving such a signal, the primary device may warn its user that the remote device is low on power, and thus enable the user to recharge or replace the battery of the remote device before the remote device actually runs out of power. One example of such a system is a computer that employs wireless user input (UI) devices, such as a wireless mouse or keyboard. When such UI devices are low on power, a signal is communicated to the computer's processor indicating the low power condition, and the computer then displays a message to the user warning of the same. If the user subsequently fails to replace or recharge the battery promptly, the remote device continues to operate normally until it has completely run out of power. At such time, the remote device becomes incapable not only of performing its intended function but also of informing the primary device of the reason it has become inoperable.

SUMMARY

According to one aspect of the present invention, a method involves us of a first device comprising a sensor configured to sense a stimulus experienced by the first device, a controller configured to process data received from the sensor and thereby obtain processed sensor data, a transmitter configured to wirelessly transmit the processed data from the first device to a second device, and a battery configured to supply power to at least the controller and the transmitter. The first device is operated in a first operational mode in which the sensor, the controller, and the transmitter are used at least occasionally to obtain and transmit processed data to the second device. When it is determined that the battery is in a low power condition, the first device is operated in a second operational mode wherein the sensor, controller, and transmitter are not used to obtain and transmit processed sensor data to the second device, but wherein the first device at least occasionally transmits a signal to the second device that indicates a low power condition of the battery.

According to another aspect, an apparatus comprises a sensor, a controller, a transmitter, and a battery. The sensor is configured to sense a stimulus experienced by the apparatus. The controller is configured to process data received from the sensor and thereby obtain processed sensor data. The transmitter is configured to wirelessly transmit the processed sensor data from the apparatus to another device. The battery is configured to supply power to at least the controller and the transmitter. The apparatus is configured to operate in a first operational mode when a determination is made that the battery is not in a low power condition, and to operate in a second operational mode when a determination is made that the battery is in a low power condition. In the first operational mode, the sensor, the controller, and the transmitter are used at least occasionally to obtain and transmit processed sensor data to the other device. In the second operational mode, the sensor, controller, and transmitter do not obtain and transmit processed sensor data to the other device, but the apparatus at least occasionally transmits a signal to the other device that indicates a low power condition of the battery.

According to another aspect, a method involves use of a first device comprising a sensor configured to sense a stimulus experienced by the first device, a controller configured to process data received from the sensor and thereby obtain processed sensor data, a transmitter configured to wirelessly transmit the processed data from the first device to a second device, a receiver configured to receive data transmitted wirelessly from the second device to the first device, and a battery configured to supply power to at least the controller, the transmitter, and the receiver. The first device is operated in a first operational mode in which the sensor, the controller, and the transmitter are used at least occasionally to obtain and transmit processed data to the second device, and in which the receiver is used at least occasionally to receive data transmitted wirelessly from the second device. When it is determined that the battery is in a low power condition, the first device is operated in a second operational mode wherein the receiver is not used to receive data transmitted wirelessly from the second device, but wherein the transmitter is used at least occasionally to transmit a signal to the second device that indicates a low power condition of the battery.

BRIEF DESCRIPTION OF THE DRAWINGS

FIGS. 2-4 are flow charts showing examples of routines that may be executed by the controller shown in FIG. 1.

DETAILED DESCRIPTION

In some embodiments, upon detecting a "low power" condition of a remote sensor device, the mode of operation of the remote device may be changed so as to substantially reduce its rate of power consumption. The remote device may then be allowed to perform only a limited set of functions, and may continue to transmit a "low power" signal to a primary device for an extended period of time in spite of its decreased functionality. In certain embodiments, the remote device may be configured so that the only function it performs while in its "low power" mode of operation is the transmission of a signal to the primary device informing the primary device of its "low power" condition. In some embodiments, the capacity or usage of the battery may additionally be monitored to determine when the battery is soon to be in a "low power" condition and a signal is transmitted indicating such to be the case, thus enabling the user to be warned that the battery is "running low and needs to be replaced soon," or to be provided with some similar message or indication. Should the user fail to replace the battery before the "low power" condition is actually reached, the device will not simply cease working, but will change modes of operation so as to substantially reduce its power consumption and will continue to inform the user of the "lower power" condition of the battery. Accordingly, unlike with prior art remote sensor devices that cease all operations after they run out of power, a user of a device like that disclosed herein will not be left guessing as to whether the system including the remote device ceased working because the remote device ran out of power or because of some other reason, such as failure of one or more other components of the remote device or failure of one or more components of the receiving device.

Figure 1:
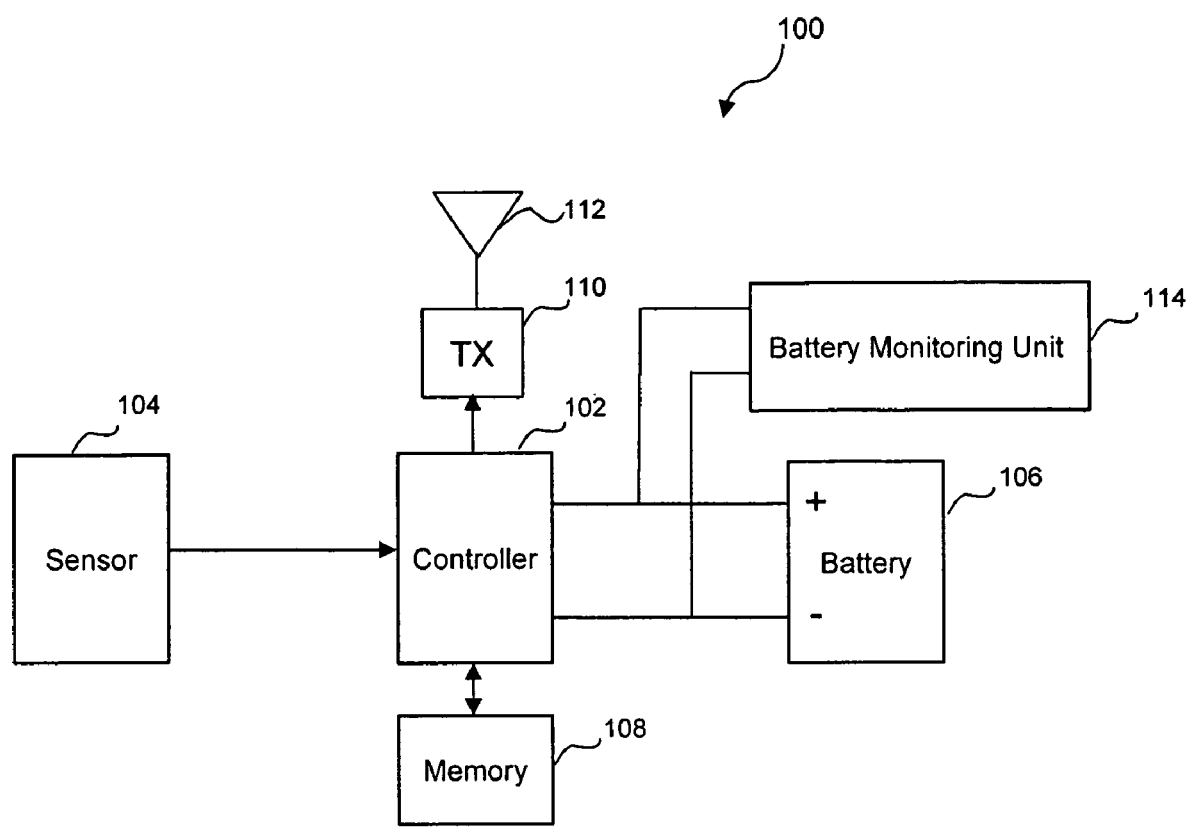
FIG. 1 is a block diagram of an illustrative embodiment of a remote sensor apparatus.

FIG. 1 is a block diagram of an example of a remote sensor device 100 that may be employed in connection with certain embodiments of the invention. As shown, the device 100 may include a controller 102, a sensor 104, a battery 106, a memory 108, a transmitter 110, an antenna 112, and a battery monitoring unit 114. A remote sensor device 100 configured generally as shown in FIG. 1 can be configured in any of a number of ways and can be used for any of a number of purposes, and the invention is not limited to any particular type of device or use thereof. In certain embodiments, for example, the remote sensor device 100 may comprise an ambulatory device that is mounted on or within a shoe or otherwise supported by a person to monitor activity of the person while he or she is walking or running or is otherwise in locomotion on foot. Examples of such devices are disclosed, for example, in U.S. Pat. Nos. 6,611,789; 6,305,221; 6,301,964; 6,298,413; 6,032,108; 6,018,705; 5,955,667; 4,578,769; and 4,371,945, the entire contents of each of which is incorporated herein by reference. Alternatively, the remote sensor device 100 may comprise, for example, a wireless mouse or a wireless keyboard for a computer, or any other device capable of sensing one or more stimuli and communicating data concerning a sensed stimulus to another device via a wireless communications link.

The sensor 104 may comprise any device that is capable of sensing an external stimulus, and the invention is not limited to the use of any particular type of sensor. It may, for example, comprise an accelerometer such as that disclosed in U.S. Pat. No. 6,336,365, which is incorporated herein by reference in its entirety, or may comprises any of the sensors disclosed in U.S. Pat. Nos. 6,611,789; 6,305,221; 6,301,964; 6,298,413; 6,032,108; 6,018,705; 5,955,667; 4,578,769; and 4,371,945. Alternatively, it may comprise, as but a few examples, another type of accelerometer, a vibration sensor, a temperature sensor, a humidity sensor, a light sensor, an audio detector, an electrical or magnetic field sensor, etc. Any number of sensors of the same type, or any combination of different types of sensors may be employed in various embodiments. It should be appreciated that the sensor 104 may additionally comprise certain signal processing elements, e.g., one or more amplifiers, buffers, filters, etc., arranged to condition a signal generated by a transducer, e.g., an accelerometer such as that disclosed in U.S. Pat. No. 6,336,365, prior to providing the signal to the controller 102.

The controller 102 may, for example, comprise one or more processors capable of receiving and processing data from the sensor 104. Any type or number of controllers may be employed and the invention is not limited to the use of a controller of any particular type or configuration. As shown in FIG. 1, the controller 102 may have an associated memory 108 in which data and instructions accessed by the controller 102 may be stored to enable the controller 102 to execute various routines. The memory 108 may be embodied either separately or integrally with the controller 102. Examples of routines that may be performed by the controller 102 in connection with certain embodiments of the invention are described below in connection with FIGS. 2-4.

The transmitter 110 and associated antenna 112 may take on any of numerous forms and may be employed, for example, to wirelessly transmit processed data from the sensor to another device, e.g., a wristwatch, a portable music player, a computer, etc. In some embodiments, a receiver (not shown) may additionally be employed in the device 100 to receive incoming wireless signals, or a transceiver, that can both transmit and receive wireless signals, may instead be used.

The battery 106 may be responsible for supplying power to all of the components in the remote device 100. It may take on any of numerous forms, and the invention is not limited to the use of a battery of any particular type or configuration. The specific type and energy capacity of the battery may be chosen based on the application at hand. In an embodiment in which the battery is used to power a shoe-mounted remote sensor device that is used to monitor performance parameters of a user in locomotion on foot, the battery may, for example, be a CR2032 Lithium coin cell having a capacity of 200 milliamp hours (mAh).

The battery monitoring unit 114 may comprise any known device or circuit capable of monitoring the remaining capacity of the battery 106. Such devices and the techniques they employ are well understood in the art and thus will not be described herein. As discussed in more detail below, in some embodiments, a "low power" condition of the battery 106 may be determined not by directly monitoring a state of the battery, but rather based upon monitoring or estimating the cumulative power consumption of the components in the device 100. Accordingly, at least in some embodiments, a battery monitoring unit 114 like that shown would not be required.

Figure 2:
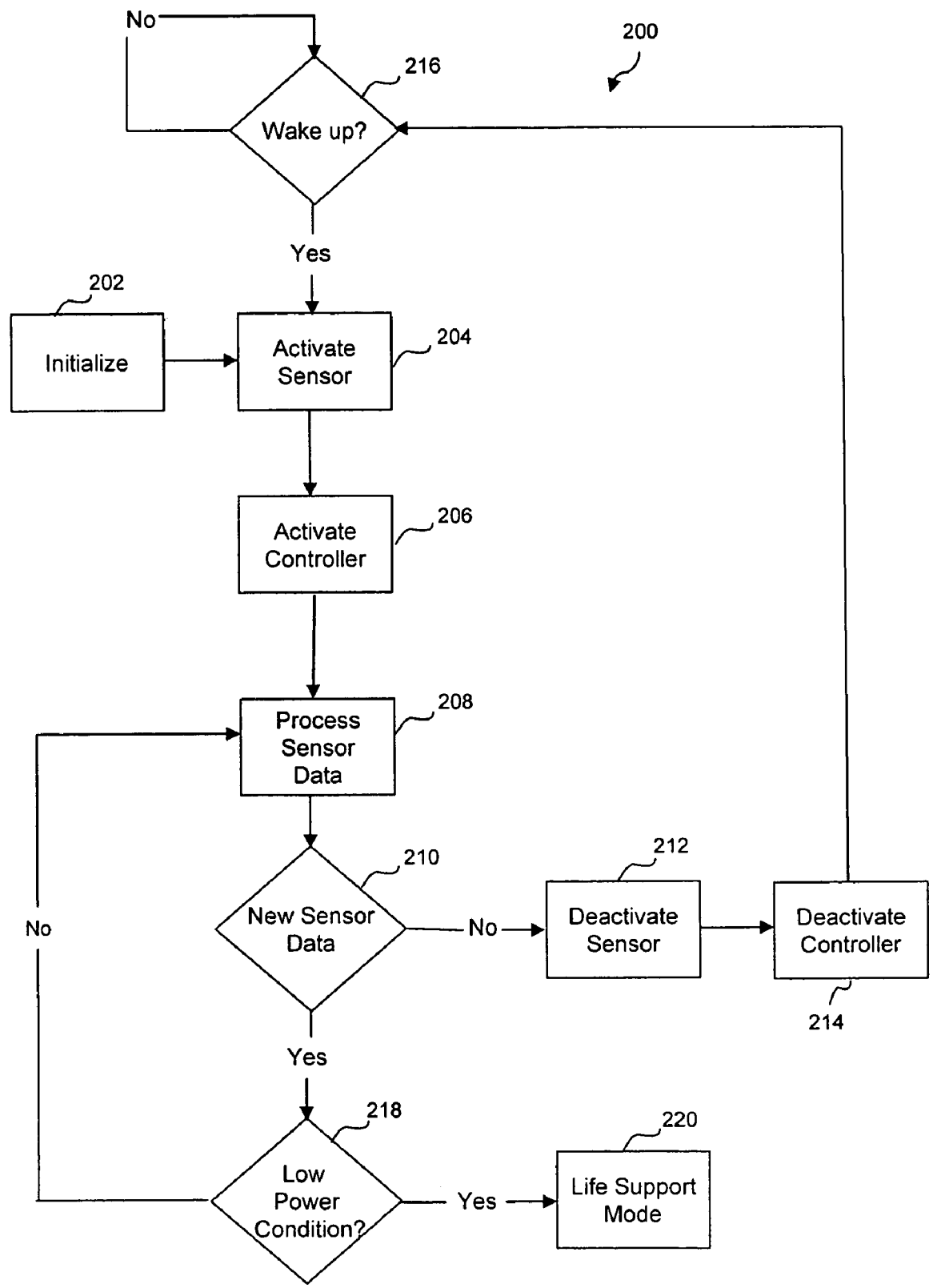

FIG. 2 shows an illustrative example of a routine 200 that may be executed by the controller 102 shown in FIG. 1. As noted above, instructions for the routine 200 may, for example, be stored in the memory 108 associated with the controller 102. As shown, the routine 200 may begin at a step 202 wherein the controller is "initialized." Such initialization may occur, for example, when a new battery 106 is installed in the device 100, in response to a user command, or by some other mechanism.

After initialization, the routine 200 proceeds to steps 204 and 206, wherein one or more sensors and controllers are placed in an "active" mode to enable them to perform their data accumulation and processing functions. In some embodiments, for example, an accelerometer and a processor may be caused to begin actively accumulating and analyzing data concerning footsteps taken by a user in locomotion on foot. It should be appreciated, however, that in certain embodiments, the step 204 may involve the activation of one or more signal processing elements, e.g., amplifiers, buffers, filters, etc., associated with a transducer (not shown) in addition to or in lieu of activating the transducer itself. It should further be appreciated that, in some embodiments a sensor may be employed that does not itself consume power, and the step 204 may thus be omitted in such embodiments.

After "activating" the sensor 104 (if necessary) and the controller 102, the routine 200 proceeds to a step 208, wherein data accumulated by the sensor may be processed in an appropriate fashion. As discussed in more detail below, in connection with the step 208, processed data from the sensor 104 may be transmitted wirelessly to another device via the transmitter 110 and antenna 112 of the device 100.

At the step 210, the routine 200 next determines whether any new data is being accumulated by the sensor 104. Such a determination may, for example, involve an assessment of whether the sensor 104 has ceased generating a signal or data for more than a particular period of time, e.g., several seconds. When it is determined that the sensor has ceased accumulating data, the routine 200 proceeds to steps 212 and 214, wherein the one or more sensors and controllers may be taken out of their "active" mode and placed in a "sleep" mode for power preservation purposes. As noted above, in embodiments in which the sensor 104 does not require power in order to be "active," the step 212 may be omitted.

After placing the device 100 in a "sleep" mode, the routine 200 waits at a step 216 until a determination is made that the device should "wake up" to begin actively processing and accumulating data once again. The determination of whether and when to wake up may be made, for example, by monitoring an output of the sensor 104 (or a transducer included therein) for activity, in a response to a user input, e.g., depression of a "start" button, or by any other mechanism. In embodiments in which a sensor is used to monitor locomotion of a person on foot, the "wake up" determination 216 may be made, for example, by employing a low-power comparator (not shown) to monitor the output of a transducer. In embodiments in which an accelerometer that does not consume power, e.g., the accelerometer disclosed in U.S. Pat. No. 6,336,365, is employed as the transducer, the power consumption of the device 100 in the "sleep" mode may thus be substantially limited to only the power consumption of such a comparator. It should be appreciated that in addition to such an automated "wake up" function, the device 100 may additionally or alternatively comprise one or more user input devices, e.g., switches or pushbuttons, that may be manipulated to cause the device 100 to "wake up." Furthermore, one or more user input devices may additionally or alternatively be provided that can be manipulated to cause the device 100 to be put into a "sleep" mode, or even to cause the device to be powered down completely so that even the automated "wake up" function is disabled until further user input is provided.

Referring again to FIG. 2, when at the step 210 (discussed above) it is determined that new data is being accumulated by the sensor 104, the routine 200 proceeds to a step 218, wherein it is determined whether the battery 106 is in a "low power" condition, e.g., by determining whether the capacity of the battery 106 has been depleted below a particular level. When, it is determined that the battery is not in a "low power" condition, the routine 200 returns to the step 208, wherein the sensor data continues to be accumulated and processed. When, it is determined that the battery 106 is in a "low-power" condition, however, the routine 200 proceeds to a step 220, wherein the device is placed in a "life support mode" (discussed in more detail below in connection with FIG. 4.) In alternative embodiments, the step 218 may additionally or alternatively be performed at other points in the routine 200, and it is not critical that it be performed immediately after determining whether new sensor data is being accumulated. For example, in some embodiments, the step 218 may additionally or alternatively be performed immediately after the step 206 and/or between the steps 208 and 210.

The determination of whether the battery 106 is in a "low power" condition may be made in any of a number of ways, and the invention is not limited to any particular technique or mechanism for making such a determination. In some embodiments, the remaining capacity of the battery 106 may be measured directly by the battery monitoring unit 114 capacity monitoring techniques that may be employed by the battery monitoring unit are well known in the art and thus will not be described in further detail. The determination of whether the battery 106 is in a "low power" condition may thus be made by evaluating whether the measured remaining capacity is below a particular threshold. In other embodiments, the controller 102 or some other device may additionally or alternatively track the cumulative power consumption of the various components in the device 100, or estimate such consumption based on cumulative time of use in various modes, and the determination of whether the battery 106 is in a "low power" condition may thus be made by evaluating whether the determined total power usage since installation of a new battery is above a particular threshold.

No matter how the "low power" determination is made, a threshold level may be set that allocates the total power capacity of the battery 106 between a first period in which the device 100 is in its "operational mode" and a second, subsequent period during which the device 100 is in its "life support mode," so as to achieve desired operational objectives. For instance, if it is desired that the device 100 be capable of transmitting a "life support beacon" once every hour for a period of two years after the primary functionality of the device has been shut down, then the threshold level may be set accordingly. The portion of the total capacity of the battery 106 that is to be used for "life support" may be calculated, for example, by multiplying the desired total number of "life support beacons" by the power consumed by each beacon transmission. The allocation of the total capacity of the battery may also, of course, take into account the desired lifetime of the device 100 in its "operational mode."

It should be appreciated that, in addition to determining whether the "low power" condition discussed above has been reached, the capacity or usage of the battery may additionally be monitored to determine when the battery is soon to be in the "low power" condition. This may be achieved, for example, by employing the same technique used to monitor for the "low power" condition, but using a slightly higher or lower threshold. When such a determination is made, a signal may be transmitted via the transmitter 110 and antenna 112 that informs the primary device that the battery 106 is running low and needs to be replaced. The message or indication provided to the user as a result of such a signal may either be the same as that provided in response to the low power beacon, or may be a different message. For example, in response to a signal indicating the battery is approaching the "low power" condition, a message may be displayed informing the user the battery is "running low," whereas in response to a signal indicating the "low power" condition has already been reached, the message may inform the user that the battery is "out of power."

FIG. 3 shows an illustrative example of the routine 208 (FIG. 2) that may be employed by a device that senses activity of a person in locomotion on foot, for example, by employing one or more accelerometers to monitor motion of the person. In the illustrative example shown, the routine 208 begins at a step 302, wherein "foot contact times" of a person, i.e., amounts of time during in which a person's foot is on the ground during respective footsteps taken by the person, are determined by examining the output of the sensor 104. Based on the measured foot contact times, the routine 208 may then calculate performance parameters such as pace, distance traveled, speed, etc., (step 304), and subsequently transmit such information to another device via the transmitter 110 and antenna 112 (step 306). The routine 208 shown in FIG. 3 is, of course, but only one example of a routine that may employed to accumulate, process, and transmit sensor data to another device. Other examples of additional or alternative routines that may be employed in connection with various embodiments of the invention are disclosed in U.S. Pat. Nos. 6,611,789; 6,305,221; 6,301,964; 6,298,413; 6,032,108; 6,018,705; 5,955,667; 4,578,769; and 4,371,945, discussed above. A radio transmission protocol such as that disclosed in U.S. Patent Application Publication No. 2002/0091785A1, or any other suitable protocol, may be employed to communicate data and/or commands between the device 100 and the other device. In some embodiments, a routine 208 such as that illustrated in FIG. 3 will be performed only when the device 100 is in its "operational mode," and may, for example, require the battery 106 to supply approximately two milliamps of current to the various components of the device 100.

FIG. 4 shows an illustrative example of a routine that may be employed when the device 100 is placed in a "life support mode" (step 200 in FIG. 2). In the example shown, the only activity for which the device 100 is allowed to consume power is to transmit a "life support beacon," e.g., a signal indicating that the device has run out of power, at least occasionally. Such a "life support" routine may, for example, require the battery 106 to supply approximately 6 microamps of current to the various components of the device 100. It should be appreciated, however, that the device 100 may alternatively be configured so that some additional level of activity beyond the transmission of a "life support beacon" may be permitted. All that is important is that the modality of the device 100 be changed in some way so that certain power-consuming activities cease when the device 100 enters the "life support mode." In some embodiments, when the device 100 is placed in its "life support mode," the modality of the radio transmission protocol employed by the device 100 may also changed so as to further minimize its power consumption. For example, in embodiments in which a two-way radio transmission protocol is employed to wirelessly communicate data between the device 100 and another device when the device 100 is in its "operational mode," the device 100 may further conserve power by switching to a one-way radio transmission protocol, e.g., to allow only the transmission of a "life-support beacon" but not the receipt of incoming messages, upon entering its "life support mode."

In the example of FIG. 4, the routine 220 first involves de-activating the sensor 104 and/or the processor 102 (steps 402 and 404) so that the controller 102 ceases processing data accumulated by the sensor 104 and transmitting processed sensor data via the transmitter 110 and antenna 112. In the example shown, the controller 102 may be deactivated except to the extent necessary to transmit a life support beacon each time the device 100 "wakes up" for such a purpose. As noted above, some embodiments may employ a sensor 104 that need not be deactivated, and the step 402 need not be employed in such circumstances.

The "wake up" step 408 may involve, for example, waking up once every minute, once every ten minutes, once every hour, etc., with a period depending upon the type of sensor that is employed and the use to which it is being put. Additionally or alternatively, the step 408 may involve sensing an external stimulus, for example, sensing motion that indicates that perhaps a user is attempting to put the device to use. In some embodiments, for example, an output of an accelerometer may be monitored to determine whether the signal exceeds a certain threshold. In certain such embodiments, power consumption in the "life support mode" may be limited significantly by basing the wake up decision in whole or in part upon the output of a low-power comparator that compares the output of an accelerometer such as that disclosed in U.S. Pat. No. 6,336,365 to a threshold voltage.

The step 408 may additionally or alternatively involve the manipulation of a user input mechanism, e.g., a pushbutton, that may cause the device to transmit a beacon upon activation of the mechanism, or may simply allow the device to "wake up" in response to a sensed stimulus and/or periodically (as discussed above), for some period of time after the mechanism has been activated. In some embodiments, a low-power receiver may additionally or alternatively be used to determine whether and when another device is attempting to communicate with the remote device 100, and the "life support beacon" may be transmitted upon detection of such a communication attempt. Any combination of the above techniques may also be employed. For example, the device may attempt to send a message once every minute during time periods after a pushbutton has been depressed or after a determination is made that the device 100 is in motion.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A method of controlling power consumption in an electronic device, comprising steps of:
  (a) providing a first device for attachment to a user, the first device comprising a sensor configured to sense a stimulus experienced by the first device, a controller configured to process data received from the sensor and thereby obtain processed sensor data, a transmitter configured to wirelessly transmit the processed data from the first device to a second device, and a battery configured to supply power to at least the controller and the transmitter, wherein the first device performs a plurality of functions including transmitting data relating to at least one performance parameter of the user based on the stimulus sensed by the sensor;
  (b) operating the first device in a first operational mode in which the sensor, the controller, and the transmitter are used at least occasionally to obtain and transmit processed data to the second device, wherein the first operational mode causes the first device to operate with a first power consumption, wherein the operating step includes:
    1) calculating a performance parameter of a user of the first device based on the signal received from the sensor,
    2) transmitting data indicative of the calculated performance parameter from the first device to the second device;
  (c) determining whether the battery is in a low power condition; and
  (d) when it is determined that the battery is in a low power condition, operating the first device in a second operational mode wherein the sensor, controller, and transmitter are not used to obtain and transmit processed sensor data to the second device, but wherein the first device at least occasionally transmits a signal to the second device that indicates a low power condition of the battery, wherein the second operational mode causes the first device to operate with a second power consumption corresponding to substantially lower power than the first power consumption;
    wherein the at least one of the plurality of functions that includes transmitting data relating to at least one performance parameter of the user includes a first function that is operational in the first operational mode and wherein the first function ceases to operate in the second operational mode.

2. The method of claim 1, wherein the step (c) comprises determining whether the battery is in a low power condition by determining whether the battery is in the low power condition by determining whether the remaining capacity of the battery is below a particular value.

3. The method of claim 1, wherein the step (c) comprises determining whether the battery is in the low power condition by determining whether the first device has consumed more than a particular amount of power from the battery.

4. The method of claim 1, wherein the steps (b)-(d) are performed with the first device while the first device is being carried by a person in locomotion on foot.

5. The method of claim 1, wherein the step (d) comprises periodically transmitting the signal that indicates the low power condition of the battery to the second device.

6. The method of claim 1, wherein the step (d) comprises transmitting the signal that indicates the low power condition of the battery to the second device in response to a stimulus detected by a transducer.

7. The method of claim 1, wherein the step (d) comprises transmitting the signal that indicates the low power condition of the battery to the second device in response to a user input.

8. The method of claim 1, further comprising steps of:
(e) determining when the battery is approaching the low power condition; and
(f) transmitting a signal to the second device that indicates the battery is approaching the low power condition.

9. An apparatus for attachment to a user, comprising:
a sensor configured to sense a stimulus experienced by the apparatus;
a controller configured to process data received from the sensor and thereby obtain processed sensor data;
a transmitter configured to wirelessly transmit the processed sensor data from the apparatus to another device; and
a battery configured to supply power to at least the controller and the transmitter;
wherein the apparatus operates in a first operational mode when a determination is made that the battery is not in a low power condition, wherein the first operational mode causes the apparatus to operate with a first power consumption, and wherein the apparatus operates in a second operational mode when a determination is made that the battery is in a low power condition, wherein the second operational mode causes the apparatus to operate with a second power consumption corresponding to substantially lower power than the first power consumption, and wherein, in the first operational mode, the sensor, the controller, and the transmitter are used at least occasionally to obtain and transmit processed sensor data to the other device, and in the second operational mode, the sensor, controller, and transmitter do not obtain and transmit processed sensor data to the other device, but the apparatus at least occasionally transmits a signal to the other device that indicates a low power condition of the battery; and
wherein the apparatus performs a plurality of functions including transmitting data relating to a performance parameter of the user based on the stimulus sensed by the sensor to the another device, and wherein the at least one of the plurality of functions including transmitting data relating to at least one performance parameter of the user includes a first function that is operational in the first operational mode and wherein the first function ceases to operate in the second operational mode.

10. The apparatus of claim 9, further comprising means for determining whether the battery is in the low power condition.

11. The apparatus of claim 9, wherein the controller is configured to determine the performance parameter of a user of the apparatus while the apparatus is in the first operational mode but not while the apparatus is in the second operational mode.

12. The apparatus of claim 9, wherein, when the apparatus is in the second operational mode, the apparatus periodically transmits the signal that indicates the low power condition of the battery to the other device.

13. The apparatus of claim 9, wherein, when the apparatus is in the second operational mode, the apparatus transmits the signal that indicates the low power condition of the battery to the other device in response to a stimulus detected by a transducer.

14. The apparatus of claim 9, wherein, when the apparatus is in the second operational mode, the apparatus transmits the signal that indicates the low power condition of the battery to the other device in response to a user input.

15. The apparatus of claim 9, further comprising:
means for determining when the battery is approaching the low power condition; and
means for transmitting a signal to the second device that indicates the battery is approaching the low power condition.

16. A method of controlling power consumption in an electronic device, comprising steps of:
(a) providing a first device for attachment to a user, the first device comprising a sensor configured to sense a stimulus experienced by the first device, a controller configured to process data received from the sensor and thereby obtain processed sensor data, a transmitter configured to wirelessly transmit the processed data from the first device to a second device, a receiver configured to receive data transmitted wirelessly from the second device to the first device, and a battery configured to supply power to at least the controller, the transmitter, and the receiver, wherein the first device performs a plurality of functions including transmitting data relating to at least one performance parameter of the user based on the stimulus sensed by the sensor;
(b) operating the first device in a first operational mode, wherein the first operational mode causes the first device to operate with a first power consumption, in which the sensor, the controller, and the transmitter are used at least occasionally to obtain and transmit processed data to the second device, and in which the receiver is used at least occasionally to receive data transmitted wirelessly from the second device;
(c) determining whether the battery is in a low power condition; and
(d) when it is determined that the battery is in a low power condition, operating the first device in a second operational mode, wherein the second operational mode causes the apparatus to operate with a second power consumption corresponding to substantially lower power than the first power consumption, wherein the receiver is not used to receive data transmitted wirelessly from the second device, but wherein the transmitter is used at least occasionally to transmit a signal to the second device that indicates a low power condition of the battery;
wherein at least one of the plurality of functions that includes transmitting data relating to at least one performance parameter of the user includes a first function that is operational in the first operational mode and wherein the first function ceases to operate in the second operational mode.

17. The method of claim 16, wherein the step (c) comprises determining whether the battery is in the low power condition by determining whether the remaining capacity of the battery is below a particular value.

18. The method of claim 16, wherein the step (c) comprises determining whether the battery is in the low power condition by determining whether the first device has consumed more than a particular amount of power from the battery.

19. The method of claim 16, wherein a transceiver is employed as both the transmitter and the receiver.

* * * * *